(12) United States Patent
Suzuki

(10) Patent No.: US 10,231,708 B2
(45) Date of Patent: Mar. 19, 2019

(54) ULTRASOUND TRANSDUCER AND ULTRASOUND DIAGNOSTIC APPARATUS

(71) Applicant: Konica Minolta, Inc., Tokyo (JP)

(72) Inventor: Kenji Suzuki, Tokyo (JP)

(73) Assignee: KONICA MINOLTA, INC., Tokyo (JP)

( * ) Notice: Subject to any disclaimer, the term of this patent is extended or adjusted under 35 U.S.C. 154(b) by 915 days.

(21) Appl. No.: 14/801,349

(22) Filed: Jul. 16, 2015

(65) Prior Publication Data

US 2016/0027991 A1 Jan. 28, 2016

(30) Foreign Application Priority Data

Jul. 28, 2014 (JP) .................................. 2014-153018

(51) Int. Cl.
*H01L 41/09* (2006.01)
*A61B 8/08* (2006.01)
(Continued)

(52) U.S. Cl.
CPC .......... *A61B 8/5207* (2013.01); *A61B 8/4494* (2013.01); *B06B 1/0622* (2013.01);
(Continued)

(58) Field of Classification Search
CPC ..... A61B 8/5207; A61B 8/4494; A61B 8/145; A61B 8/461; B06B 1/0622; H01L 27/20; H01L 41/0973
(Continued)

(56) References Cited

U.S. PATENT DOCUMENTS

| 2002/0105250 A1* | 8/2002 | Klee | B06B 1/0622 |
| | | | 310/365 |
| 2006/0238067 A1* | 10/2006 | Dausch | B06B 1/0622 |
| | | | 310/311 |

(Continued)

FOREIGN PATENT DOCUMENTS

JP 2014017565 A 1/2014

OTHER PUBLICATIONS

D.E. Dausch, et al; Piezoelectric micromachined ultrasound transducer (pMUT) arrays for 3D imaging probes; Proceedings of the IEEE Ultrasounds Symposium; vol. 1; 2006; pp. 930-933.

*Primary Examiner* — Thomas M Dougherty
(74) *Attorney, Agent, or Firm* — Lucas & Mercanti, LLP

(57) ABSTRACT

An ultrasound transducer that achieves broadband characteristics without degrading the sensitivity of the ultrasound transducer. Piezoelectric element (202) includes piezoelectric thin film (203), first electrode (204) that is disposed on a first surface of piezoelectric thin film (203) in a thickness direction of piezoelectric thin film (203), and second electrode (205) that is disposed on a second surface of piezoelectric thin film (203) in the thickness direction of piezoelectric thin film (203), and at least two of parameters of a spring constant, a viscosity coefficient, and a mass in an equivalent single damped oscillation model representing a structure of a diaphragm composed of each piezoelectric cell (200) are each set to a value that is different among the piezoelectric cells (200) such that a relationship between a driving frequency ratio and a phase in the diaphragm is substantially identical among the piezoelectric cells (200).

11 Claims, 14 Drawing Sheets

(51) Int. Cl.
   *A61B 8/00*    (2006.01)
   *B06B 1/06*    (2006.01)
   *H01L 27/20*   (2006.01)
   *A61B 8/14*    (2006.01)

(52) U.S. Cl.
   CPC .......... *H01L 27/20* (2013.01); *H01L 41/0973* (2013.01); *A61B 8/145* (2013.01); *A61B 8/461* (2013.01)

(58) Field of Classification Search
   USPC .................. 310/311, 320, 322, 324, 334
   See application file for complete search history.

(56) References Cited

U.S. PATENT DOCUMENTS

| | | | |
|---|---|---|---|
| 2010/0327695 A1* | 12/2010 | Goel ................. | B06B 1/0622 310/320 |
| 2011/0291207 A1* | 12/2011 | Martin ............... | G10K 9/125 257/416 |
| 2012/0319535 A1* | 12/2012 | Dausch .............. | B06B 1/0622 310/365 |
| 2014/0010388 A1 | 1/2014 | Akiyama et al. | |
| 2014/0219063 A1* | 8/2014 | Hajati ............... | B06B 1/0292 367/157 |

* cited by examiner

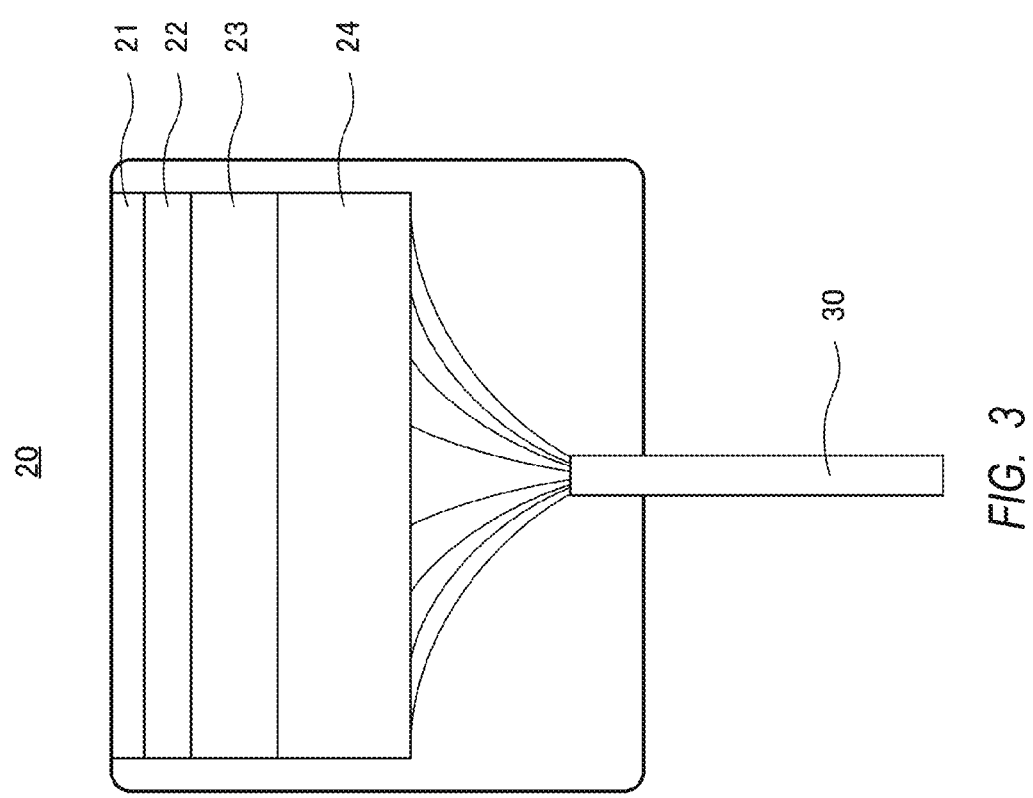

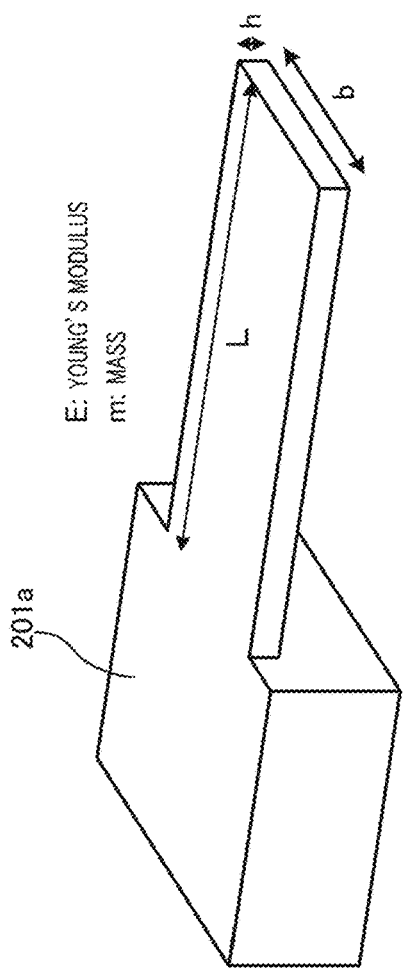

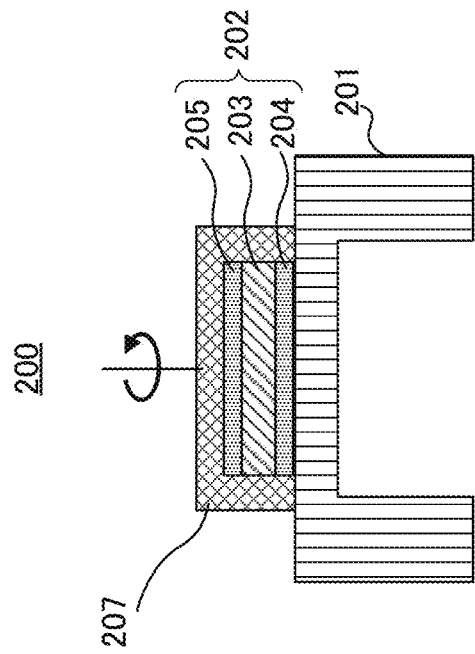
FIG. 9B
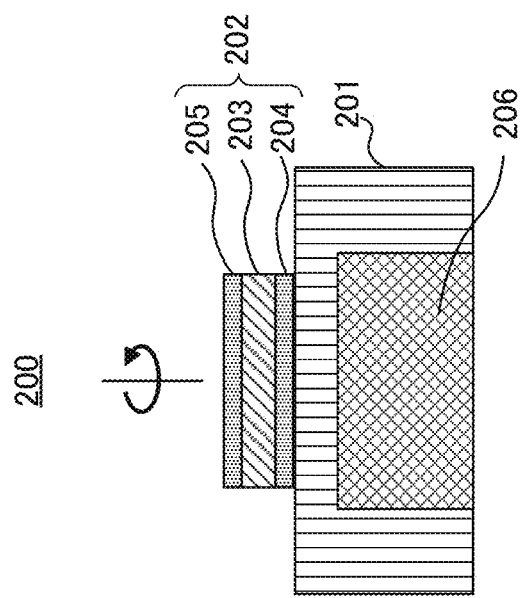
FIG. 9A
| INCREASED PARAMETER | CONTRIBUTION TO $\zeta$ |
|---|---|
| c | POSITIVE |
FIG. 9C

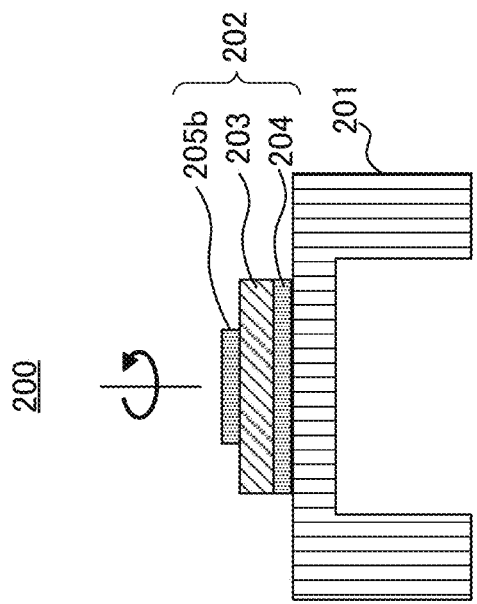
FIG. 10A
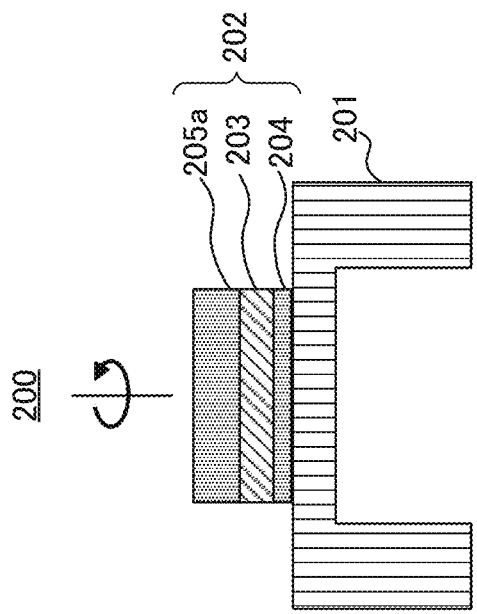
FIG. 10B
| INCREASED PARAMETER | CONTRIBUTION TO $\zeta$ |
|---|---|
| m | POSITIVE |
FIG. 10C

| ADJUSTMENT OBJECT | | PARAMETER | MANAGEABILITY OF ACCURACY (ADJUSTMENT BY SHAPE, THICKNESS, ETC.) | SIMPLICITY OF STRUCTURE IN THICKNESS DIRECTION (REDUCTION IN NUMBER OF PHOTOMASKS OR LITHOGRAPHY PROCESSES) | AMOUNT OF MATERIAL | TOTAL SCORE (PRIORITY=3) |
|---|---|---|---|---|---|---|
| SPRING CONSTANT k | DIAPHRAGM SUPPORTING STRUCTURE | LENGTH L | A | A | A | 3 |
| | | HEIGHT h | A | B | A | 2 |
| | | WIDTH b | A | A | A | 3 |
| VISCOSITY COEFFICIENT c | FORMATION OF LIQUID/RESIN ON FRONT/REAR SURFACE OF DIAPHRAGM | — | B | A | — | 1 |
| MASS m | UPPER ELECTRODE 205 | AREA A | A | A | A | 3 |
| | | THICKNESS t | A | B | A | 2 |
| | | ELECTRODE MATERIAL DENSITY ρ | A | B | B | 1 |

FIG. 11

ULTRASOUND TRANSDUCER AND ULTRASOUND DIAGNOSTIC APPARATUS

CROSS REFERENCE TO RELATED APPLICATIONS

This application is entitled to and claims the benefit of Japanese Patent Application No. 2014-153018, filed on Jul. 28, 2014, the disclosure of which including the specification, drawings and abstract is incorporated herein by reference in its entirety.

TECHNICAL FIELD

The present invention relates to an ultrasound transducer and an ultrasound diagnostic apparatus.

BACKGROUND ART

In recent years, for an ultrasound transducer (also called ultrasound probe or ultrasound probe) of an ultrasound diagnostic apparatus, piezoelectric micromachined ultrasound transducers (pMUTs) utilizing a micro electro mechanical system (MEMS) have been increasingly developed (see, for example, non PTL 1).

A piezoelectric cell (transducer, which is sometimes referred to also as pMUT cell below) used in a pMUT advantageously has high-frequency suitability and high sensitivity, but has a problem of its narrowband characteristics. In contrast, for example, the ultrasound transducer disclosed in PTL 1 achieves broadband in its entirety by arranging and simultaneously driving piezoelectric cells having resonance frequencies different from one another and each having narrowband characteristics. For example, in PTL 1, the spring constants (e.g., the area, thickness, material of the oscillation film and the like) of oscillation films of piezoelectric cells are set to values different from one another to acquire different resonance frequencies.

CITATION LIST

Patent Literature

PTL 1: Japanese Patent Application Laid-Open No. 2014-017565

NPL 1: D. E. Dausch et al., "Piezoelectric Micromachined Ultrasound Transducer (pMUT) Arrays for 3D Imaging Probes," Proceedings of the IEEE Ultrasounds Symposium, vol. 1 (2006), pp. 930-933

SUMMARY OF INVENTION

Technical Problem

As described above, in PTL 1, the amplitude characteristics relating to the resonance frequency of each piezoelectric cell are adjusted with use of the spring constant of the oscillation film of each piezoelectric cell. However, the piezoelectric cell has phase characteristics as well as amplitude characteristics. Even in the case where the amplitude characteristics are adjusted as stated in PTL 1, when a plurality of piezoelectric cells having different phase characteristics are simultaneously driven, the sound pressures of the piezoelectric cells undesirably cancel each other (back-coupling is caused) when the phase is inverted. As a result, the entire output sound pressure is reduced, and consequently the sensitivity of the ultrasound transducer is degraded.

An object of the present invention is to provide an ultrasound transducer and an ultrasound diagnostic apparatus which can acquire broadband characteristics without degrading the sensitivity of the ultrasound transducer.

Solution to Problem

In an ultrasound transducer according to an aspect of the present invention in which a plurality of piezoelectric cells having resonance frequencies different from one another are arranged, the piezoelectric cells each include a piezoelectric element, and a substrate that supports the piezoelectric element, the piezoelectric element includes a piezoelectric thin film, a first electrode that is disposed on a first surface of the piezoelectric thin film in a thickness direction of the piezoelectric thin film and is joined on the substrate, and a second electrode that is disposed on a second surface of the piezoelectric thin film in the thickness direction of the piezoelectric thin film and is paired with the first electrode to apply a voltage to the piezoelectric thin film, and at least two of parameters of a spring constant, a viscosity coefficient, and a mass in an equivalent single damped oscillation model representing a structure of a diaphragm composed of each piezoelectric cell are each set to a value that is different among the piezoelectric cells such that a relationship between a driving frequency ratio and a phase in the diaphragm is substantially identical among the piezoelectric cells.

An ultrasound diagnostic apparatus according to another aspect of the present invention includes: An ultrasound transducer including an array of a plurality of piezoelectric cells having resonance frequencies different from one another; a transmission section that drives the ultrasound transducer to transmit a first ultrasound signal to a test object; a reception section that drives the ultrasound transducer to receive a second ultrasound signal from the test object in response to the first ultrasound signal; an image processing section that creates an image for ultrasound diagnosis with use of the second ultrasound signal; and a display section that displays the image created by the image processing section. The piezoelectric cells each include a piezoelectric element, and a substrate that supports the piezoelectric element, and the piezoelectric element include a piezoelectric thin film, a first electrode that is disposed on a first surface of the piezoelectric thin film in a thickness direction of the piezoelectric thin film and is joined on the substrate, and a second electrode that is disposed on a second surface of the piezoelectric thin film in the thickness direction of the piezoelectric thin film and is paired with the first electrode to apply a voltage to the piezoelectric thin film, and at least two of parameters of a spring constant, a viscosity coefficient, and a mass in an equivalent single damped oscillation model representing a structure of a diaphragm composed of each piezoelectric cell are each set to a value that is different among the piezoelectric cells such that a relationship between a driving frequency ratio and a phase in the diaphragm is substantially identical among the piezoelectric cells.

Advantageous Effects of Invention

According to the present invention, without degrading the sensitivity of an ultrasound transducer, broadband characteristics can be achieved.

BRIEF DESCRIPTION OF DRAWINGS

FIG. 3 illustrates an internal configuration of an ultrasound transducer according to the present disclosure;

FIGS. 8A and 8B are an enlarged view and an explanatory view of a configuration of the pMUT cell in the case where the spring constant is adjusted according to the present disclosure;

FIGS. 9A to 9C illustrate a configuration of the pMUT cell in the case where a viscosity coefficient is adjusted according to the present disclosure;

FIGS. 10A to 10C illustrate a configuration of the pMUT cell in the case where a mass is adjusted according to the present disclosure;

FIG. 11 shows evaluations on parameters used for adjustment of phase characteristics according to the present disclosure;

DESCRIPTION OF EMBODIMENTS

Figure 1:
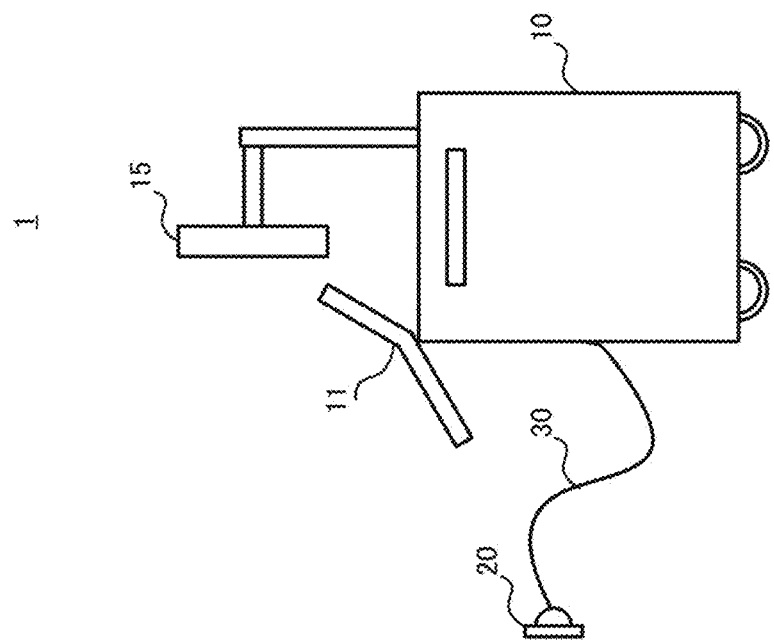
FIG. 1 illustrates a general configuration of an ultrasound diagnostic apparatus according to the present disclosure.

In the following, an ultrasound transducer and an ultrasound diagnostic apparatus according to an embodiment of the present disclosure will be described with reference to the drawings. It is to be noted that, in the embodiment, the same components (sequence for the same operation) are denoted by the same reference numerals, and reiterated descriptions will be omitted.

[Configuration of Ultrasound Diagnostic Apparatus]

Figure 2:
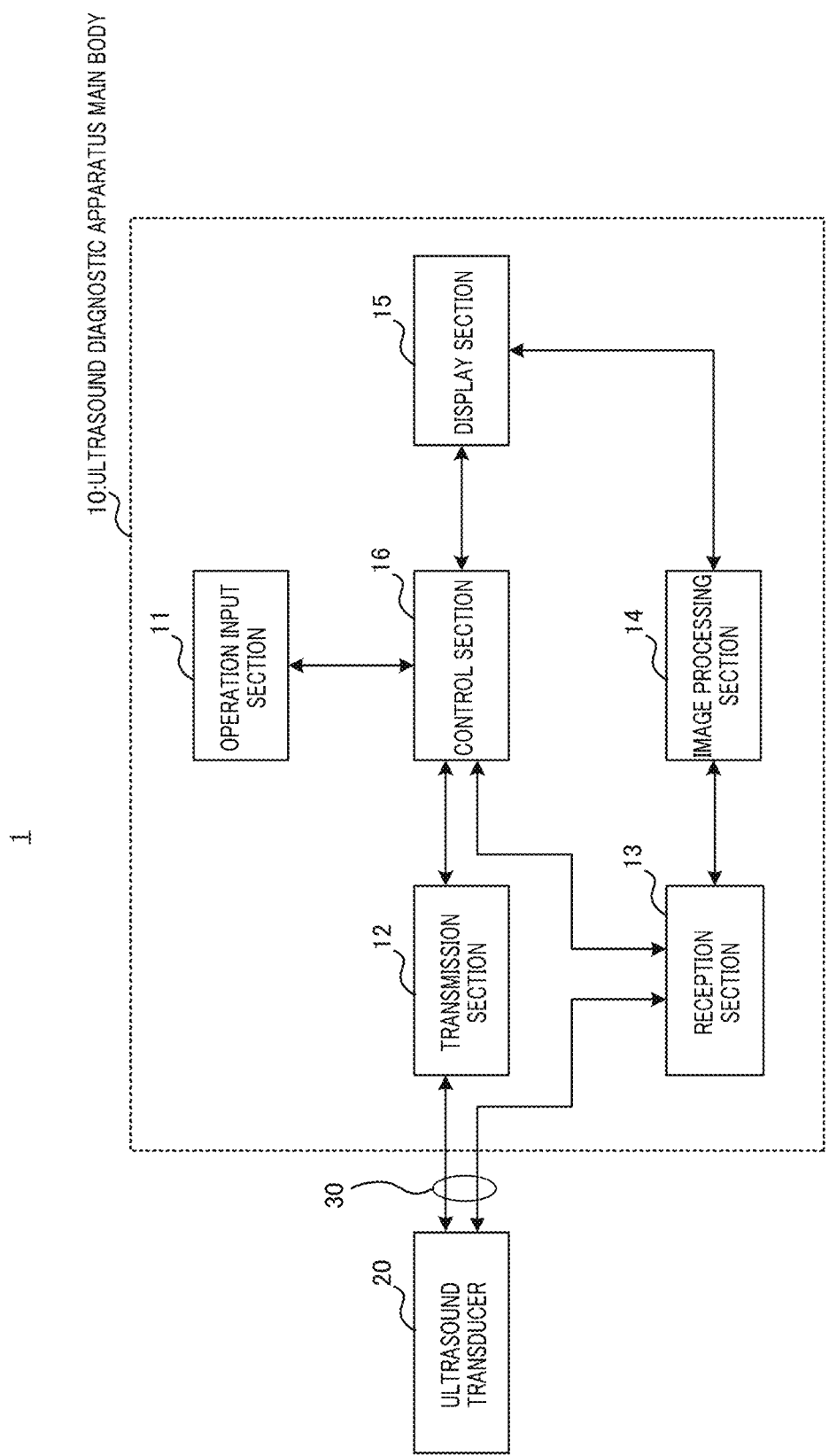
FIG. 2 is a block diagram illustrating a configuration of the ultrasound diagnostic apparatus according to the present disclosure.

FIG. 1 illustrates a general configuration of the ultrasound diagnostic apparatus having the ultrasound transducer according to the present embodiment. FIG. 2 is a block diagram illustrating an electrical configuration of the ultrasound diagnostic apparatus according to the present embodiment.

Ultrasound diagnostic apparatus 1 includes ultrasound diagnostic apparatus main body 10, ultrasound transducer 20, and cable 30.

Ultrasound transducer 20 transmits an ultrasound signal to a human body (not illustrated) as a test object, and receives an ultrasound signal which corresponds to the ultrasound waves and comes from the human body. In ultrasound transducer 20, a plurality of pMUT cells (described later) having resonance frequencies different from one another are arranged.

Ultrasound diagnostic apparatus main body 10 is connected with ultrasound transducer 20 through cable 30, and transmits a transmission signal in the form of an electric signal to ultrasound transducer 20 through cable 30 to control ultrasound transducer 20 to transmit an ultrasound signal. With use of an electric signal generated in ultrasound transducer 20 based on the ultrasound signal received by ultrasound transducer 20, ultrasound diagnostic apparatus main body 10 creates an ultrasound image of the internal state of the human body.

To be more specific, ultrasound diagnostic apparatus main body 10 includes operation input section 11, transmission section 12, reception section 13, image processing section 14, display section 15, and control section 16.

Operation input section 11 is used to input a command requesting the start of diagnosis or to input information relating to a test object, for example. Operation input section 11 is a keyboard or an operation panel provided with a plurality of input switches, for example.

Transmission section 12 transmits a control signal received from control section 16 to ultrasound transducer 20 through cable 30. That is, transmission section 12 drives ultrasound transducer 20 to transmit an ultrasound signal to a test object.

Reception section 13 receives a reception signal transmitted from ultrasound transducer 20 through cable 30. That is, reception section 13 drives ultrasound transducer 20 to receive an ultrasound signal from the test object which corresponds to the transmitted ultrasound signal. Then, reception section 13 outputs the received ultrasound signal to image processing section 14.

Under the instruction of control section 16, image processing section 14 generates an image (ultrasound image) for ultrasound diagnosis that represents the internal state of the test object with use of the ultrasound signal received from reception section 13.

Under the instruction of control section 16, display section 15 displays the ultrasound image generated in image processing section 14.

Control section 16 controls operation input section 11, transmission section 12, reception section 13, image processing section 14, and display section 15 in accordance with their functions to control the entirety of ultrasound diagnostic apparatus 1.

[Configuration of Ultrasound Transducer]

FIG. 3 illustrates an exemplary basic configuration of ultrasound transducer 20 according to the present embodiment. Ultrasound transducer 20 illustrated in FIG. 3 includes protective layer 21, ultrasound exchange section 22, bucking material 23, and signal processing circuit 24.

Protective layer 21 is formed of silicone rubber or the like and configured to cover ultrasound exchange section 22 such that uncomfortable feeling is not applied when it is brought into contact with a human body, for example.

Ultrasound exchange section 22 is provided between protective layer 21 and bucking material 23, and configured to transmit and receive ultrasound waves. Ultrasound exchange section 22 includes a plurality of pMUT cells (described later).

Bucking material 23 reduces unnecessary oscillation generated in ultrasound exchange section 22.

Signal processing circuit 24 is connected with ultrasound diagnostic apparatus main body 10 through cable 30, and generates a pulsed signal for ultrasound transmission, or performs processing of a pulsed reception signal.

[Configuration of pMUT Cell]

In the following, the configuration of the pMUT cell of ultrasound exchange section 22 illustrated in FIG. 3 will be described in detail.

Figure 4A:
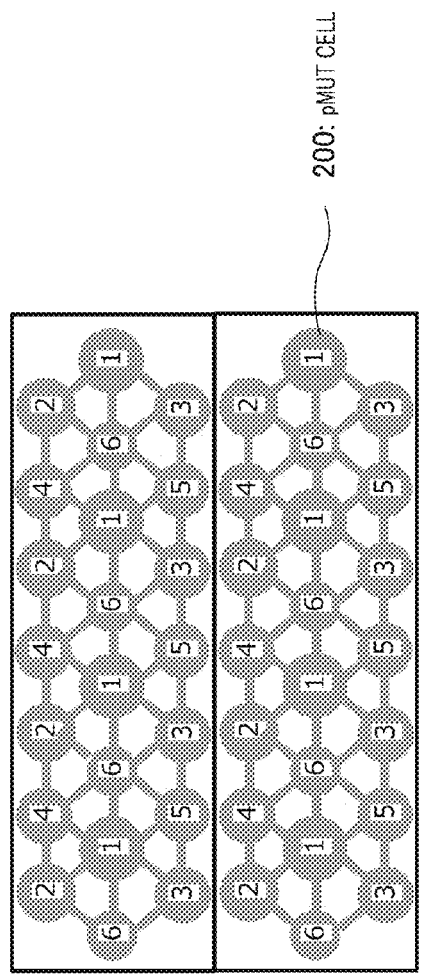
FIGS. 4A and 4B illustrate an exemplary layout of pMUT cells according to the present disclosure.
Figure 4B:
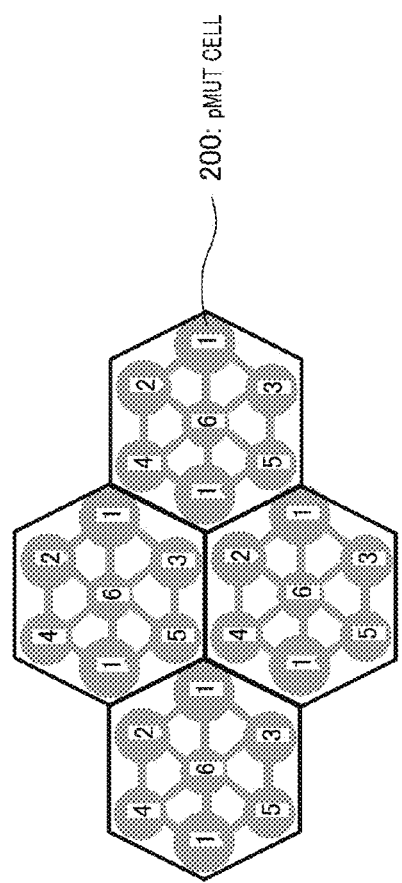

Ultrasound exchange section 22 includes a substrate, and a plurality of pMUT cells formed on the substrate. For example, as illustrated in FIG. 4A or FIG. 4B, pMUT cells 200 are arranged on the substrate, or, electrically connected in parallel. FIG. 4A illustrates an exemplary configuration of a 1D array of 2ch, and FIG. 4B illustrates an exemplary configuration of 2D array of 2ch×2ch. It should be noted that the layout of pMUT cells 200 is not limited to the configuration illustrated in FIG. 4A or FIG. 4B.

Figure 5A:
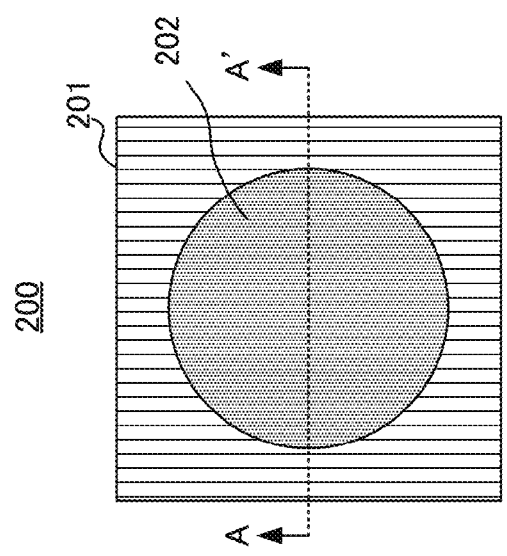
FIGS. 5A to 5C illustrate a configuration of the pMUT cell according to the present disclosure.
Figure 5B:
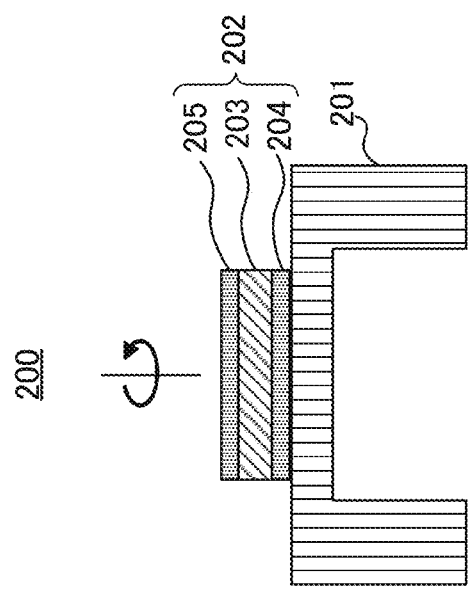
Figure 5C:
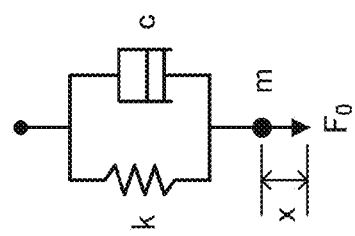

FIGS. 5A to 5C illustrate a basic structure of pMUT cell 200. FIG. 5A is a plan view of pMUT cell 200, and FIG. 5B is a sectional view taken along line A-A' of FIG. 5A. It is to be noted that electrode lines are omitted in FIG. 5A and FIG. 5B.

pMUT cell 200 is composed of piezoelectric element 202, and substrate 201 that supports piezoelectric element 202.

In addition, piezoelectric element 202 is composed of piezoelectric thin film (piezoelectric member) 203, lower electrode 204, and upper electrode 205. Lower electrode 204 is disposed on a rear surface (one surface in the thickness direction) of piezoelectric thin film 203 and is joined on substrate 201. Upper electrode 205 is disposed on a front surface (the other surface in the thickness direction) of piezoelectric thin film 203 and is paired with lower electrode 204 so as to apply a voltage to piezoelectric thin film 203.

Examples of the material of upper electrode 205 and lower electrode 204 include platinum, gold, aluminum and the like, for example.

pMUT cell 200 illustrated in FIG. 5B has a diaphragm structure in which substrate 201 serves as a supporting body, and a diaphragm composed of piezoelectric element 202 is oscillated as a drum to transmit and receive ultrasound waves.

FIG. 5C illustrates an equivalent single damped oscillation model representing a structure of the diaphragm formed by pMUT cell 200 illustrated in FIG. 5B. In FIG. 5C, k represents the spring constant of the oscillation in the diaphragm structure, c the viscosity coefficient (which is sometimes referred to also as attenuation coefficient), m the lumped mass (hereinafter sometimes referred to simply as mass), x the displacement from a reference position (extend/compress of the spring), and $F_0$ the periodical external force (i.e., the intensity of a drive signal).

The diaphragm structure (oscillation model) illustrated in FIG. 5C satisfies the following expression.

[Expression 1]

$$kx + c\frac{dx}{dt} + m\frac{d^2x}{dt^2} = F_0 \sin\varpi t \quad (1)$$

In Expression (1), ω represents the driving angular frequency (corresponding to the driving frequency if divided by 2π) of pMUT cell 200. In addition, the displacement velocity response v (in proportion to the output sound pressure) in the diaphragm structure illustrated in FIG. 5C is expressed by the following expression.

[Expression 2]

$$v = x_0 \overline{\omega} \cos(\overline{\omega} t + \beta) \quad (2)$$

In Expression (2), $x_0$ represents the maximum displacement, which is determined by the ratio of external force $F_0$ to spring constant k, and t represents the time. In addition, β represents the phase angle, which is expressed by the following expression.

[Expression 3]

$$\beta = \tan^{-1}\left(\frac{-2\kappa}{1-\kappa^2}\right)\zeta \quad (3)$$

κ (driving frequency ratio) and ζ (viscosity coefficient ratio) expressed in Expression (3) are expressed by the following Expressions (4) and (5), respectively.

[Expression 4]

$$\kappa = \frac{\varpi}{\varpi_0} \quad (4)$$

[Expression 5]

$$\zeta = \frac{c}{c_c} \quad (5)$$

In Expressions (4) and (5), $\omega_0$ represents the natural frequency (corresponding to the resonance frequency), and $c_c$ the critical viscosity coefficient (which is sometimes referred to also as critical attenuation coefficient). From Expression (3), it can be said that when κ=1 (ω=$\omega_0$, that is, at the time of driving at a resonance frequency), displacement velocity v (output sound pressure) is maximized.

In addition, the above-described k, m, and $c_c$ satisfy the following relationships. It is to be noted that ρ represents the material density of the electrode, t the thickness of the electrode, and A the area of the electrode.

[Expression 6]

$$k = m\overline{\omega}_0^2$$

$$m = \rho t A$$

$$c_c = 2\sqrt{mk} \quad (6)$$

Figure 6:
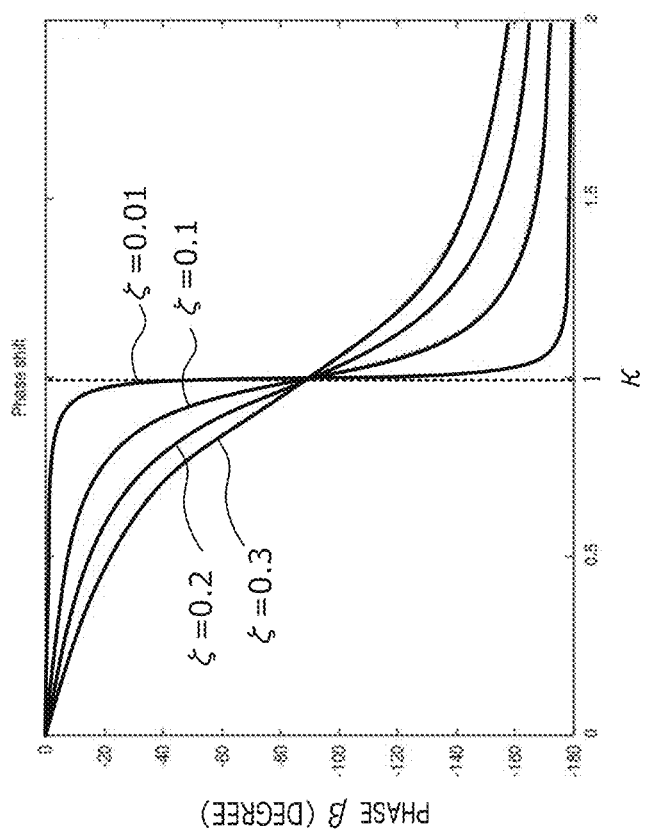
FIG. 6 shows a relationship between κ and phase β according to the present disclosure.

Here, FIG. 6 shows a relationship (phase characteristics) between variable κ and phase angle β in the case of different variables ζ. As illustrated in FIG. 6, when κ=1 (ω=$\omega_0$), phase β has the same value regardless of the values of ζ. Meanwhile, when κ is not 1, that is, in the case where κ<1 (ω<$\omega_0$) or κ>1 (ω>$\omega_0$), phase β differs depending on the value of ζ. In particular, variation of phase β near κ=1 is steep in comparison with variation of phase β near κ=0 or 2 (i.e., values sufficiently different from κ=1).

As described, when the value of ζ is different among the diaphragm structures of respective pMUT cells 200 of ultrasound exchange section 22, the phase characteristics are undesirably different among pMUT cells 200. As described above, when the phase characteristics are different among pMUT cells 200, sound pressures of pMUT cells 200 cancel each other, and consequently the sensitivity of ultrasound transducer 20 is undesirably degraded.

For this reason, in the present embodiment, the diaphragm structures of pMUT cells 200 are adjusted to substantially equalize the phase characteristics of the pMUT cells. Here, attention is paid to the expression of the relationship of ζ in Expression (5).

As expressed in Expression (6), critical viscosity coefficient $c_c$ is represented by spring constant k and mass m. That is, ζ in Expression (5) is determined by spring constant k, viscosity coefficient c, and mass m. In other words, ζ can be adjusted by changing spring constant k, viscosity coefficient c, or mass m.

Here, spring constant k is changed in accordance with the structure of the supporting body of the diaphragm of the pMUT cell 200 (i.e., substrate 201). In addition, viscosity coefficient c is changed in accordance with the friction and the viscosity of the whole surface or the back surface of the diaphragm of pMUT cell 200. In addition, mass m is changed in accordance with the structure (area, thickness, or density) of upper electrode 205 of pMUT cell 200.

In the present embodiment, for example, by changing at least two of the parameters of spring constant k, viscosity coefficient c, and mass m to adjust phase characteristics (β), the phase characteristics (i.e., ζ) of pMUT cells 200 are substantially equalized. That is, in the present embodiment, at least two of the parameters of spring constant k, viscosity coefficient c, and mass m in the equivalent single damped oscillation model representing the diaphragm structure are set to different values among pMUT cells 200 such that the relationship between κ and phase β (phase characteristics) in a diaphragm composed of pMUT cell 200 illustrated in FIG. 5C is substantially identical to one another among pMUT cells 200.

In the following, the method for adjusting the phase characteristics will be described in detail for each of spring constant k, viscosity coefficient c, and mass m.

[Spring Constant k]

Figure 7B:
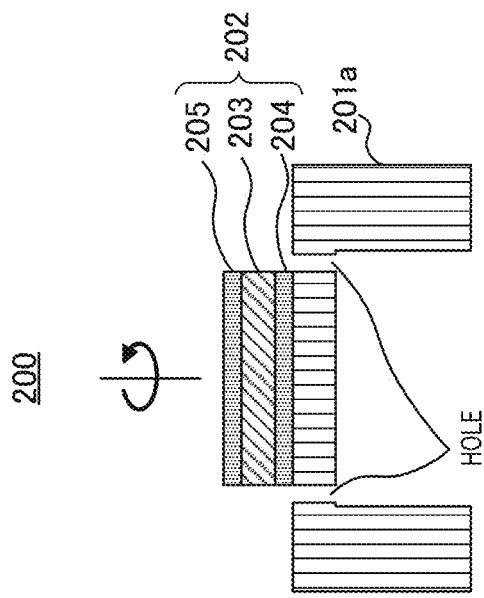
FIGS. 7A and 7B illustrate a configuration of the pMUT cell according to the present disclosure in the case where a spring constant is adjusted.
Figure 7A:
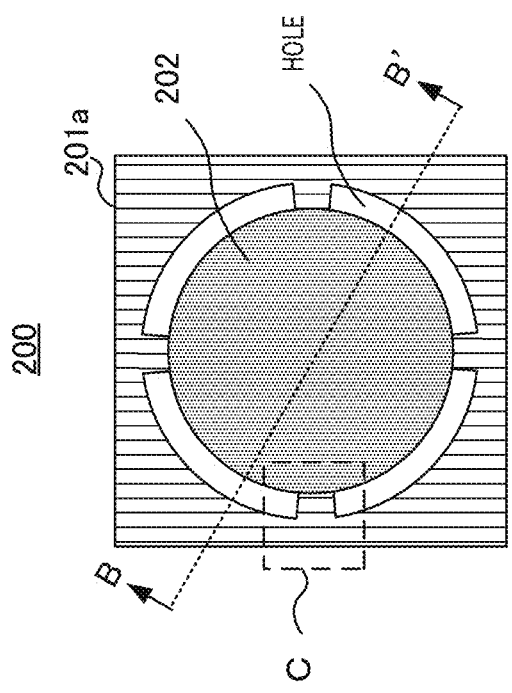

FIGS. 7A and 7B illustrate a structure of pMUT cell 200 in the case where spring constant k is adjusted. FIG. 7A is a plan view of pMUT cell 200, and FIG. 7B is a sectional view taken along line B-B' of FIG. 7A. It is to be noted that electrode lines are omitted in FIG. 7A and FIG. 7B.

As illustrated in FIG. 7A, in the surface of substrate 201a of pMUT cell 200 that makes contact with piezoelectric element 202, holes are partially formed at the outer periphery portion of piezoelectric element 202. Spring constant k is adjusted by changing the support structure of the diaphragm in each pMUT cell 200 in the above-mentioned manner to change the cross-sectional secondary moment. By adjusting the holes formed in substrate 201a as illustrated in FIG. 7A and FIG. 7B, spring constant k is adjusted without changing the diameter (which is sometimes referred to also as diaphragm diameter) of piezoelectric element 202, and as a result, viscosity coefficient ratio is adjusted. That is, the spring constant differs among pMUT cells 200 depending on the sizes of the holes illustrated in FIG. 7A and FIG. 7B.

FIG. 8A is an explanatory view of change in spring constant k according to the size of the hole. To be more specific, FIG. 8A is an enlarged perspective view of substrate 201a in region C illustrated in FIG. 7A. As illustrated in FIG. 8A, length L corresponds to the length in the radial direction of a hole formed at the outer periphery part of piezoelectric element 202, and as L is increased, the length in the radial direction of the hole is increased. In addition, width b corresponds to the length in the circumferential direction of the hole, and as b is increased, the length in the circumferential direction is reduced. In addition, height h corresponds to the thickness of substrate 201a at the circumferential part where the hole is formed. That is, the size of the hole is adjusted by adjusting the lengths of L, b and h illustrated in FIG. 8A.

As described, in pMUT cell 200 illustrated in FIG. 8A and FIG. 8B, spring constant k is adjusted by changing the shape of the diaphragm supporting body.

Here, critical viscosity coefficient $c_c$ in Expression (6) is expressed by the following expression using variables L, b and h.

[Expression 7]

$$c_c = 2\sqrt{mk} = 2\sqrt{\frac{mEbh^3}{4L^3}} \tag{7}$$

In Expression (7), m represents mass, and E the Young's modulus. Accordingly, spring constant k is expressed by the following expression using variables L, b, and h.

[Expression 8]

$$k = \frac{Ebh^3}{4L^3} \tag{8}$$

Then, variations of ζ achieved by changing variables b, h and L to adjust the diaphragm support structure are expressed by the following Expressions (9) to (11), respectively.

[Expression 9]

$$\frac{\partial \zeta}{\partial b} = \frac{\partial \zeta}{\partial c_c} \frac{\partial c_c}{\partial b} = -\frac{c}{4c_c^2}\sqrt{\frac{mEh^3}{bL^3}} < 0 \tag{9}$$

[Expression 10]

$$\frac{\partial \zeta}{\partial h} = \frac{\partial \zeta}{\partial c_c} \frac{\partial c_c}{\partial h} = -\frac{3c}{2c_c^2}\sqrt{\frac{mEbh}{L^3}} < 0 \tag{10}$$

[Expression 11]

$$\frac{\partial \zeta}{\partial L} = \frac{\partial \zeta}{\partial c_c} \frac{\partial c_c}{\partial L} = \frac{3c}{2c_c^2}\sqrt{\frac{mEbh^3}{L^5}} > 0 \tag{11}$$

From Expression (9) to (11), as illustrated in FIG. 8B, increase in width b contributes to negative change of ζ, increase in height h contributes to negative change of ζ, and increase in length L contributes to positive change of ζ.

Thus, by adjusting the diaphragm support structures among pMUT cells 200, phase characteristics (ζ) of pMUT cells 200 can be substantially equalized among pMUT cells 200.

[Viscosity Coefficient c]

FIG. 9A and FIG. 9B illustrate a structure of pMUT cell 200 in the case where viscosity coefficient c is adjusted according to the present embodiment. It is to be noted that electrode lines are omitted in FIG. 9A and in FIG. 9B.

Substrate 201 of pMUT cell 200 illustrated in FIG. 9A includes a hollow part (internal space) that is defined by projecting piezoelectric element 202 to substrate 201 in the thickness direction of piezoelectric element 202 (i.e., on the back side of the diaphragm). In the present embodiment, the internal space of substrate 201 on the back side of the diaphragm is filled with filler 206 such as fluid and resin. Examples of filler 206 include flexibility epoxy resin, silicone oils, fluoroethers, fluorocarbons, pure water and the like for example.

On the other hand, in pMUT cell 200 illustrated in FIG. 9B, an insulation layer formed of resin material 207 is formed on the front surface side of the diaphragm so as to cover piezoelectric element 202. Examples of resin material 207 include a flexible epoxy resin and the like, for example.

Specifically, in pMUT cell 200 illustrated in FIG. 9A and FIG. 9B, an insulation layer is formed or filler 206 is supplied on the side of the front surface or the back surface of the diaphragm, to adjust viscosity coefficient c. That is, in pMUT cell 200 illustrated in FIG. 9A, viscosity coefficient c differs depending on whether the internal space of substrate 201 is filled with filler 206, or depending on the material of filler 206. In addition, in pMUT cell 200 illustrated in FIG. 9B, viscosity coefficient c differs depending on the material (resin material 207) of the insulation layer.

Here, the variation of $\zeta$ in the case where viscosity coefficient c is changed in Expression (5) (Expression (7)) is expressed by the following expression.

[Expression 12]

$$\frac{\partial \zeta}{\partial c} = \frac{1}{c_c} > 0 \tag{12}$$

From Expression (12), as illustrated in FIG. 9C, increase in viscosity coefficient c caused by filler 206 or resin material 207 contributes to a positive change of $\zeta$. It is to be noted that the degree of the increase in viscosity coefficient c differs depending on the type of filler 206 or resin material 207.

By adjusting the presence/absence and the type of filler 206 or resin material 207 in this manner in each pMUT cell 200, the phase characteristics ($\zeta$) of pMUT cells 200 can be substantially equalized.

[Mass m]

FIG. 10A and FIG. 10B illustrate structures of pMUT cell 200 in the case where mass m is adjusted according to the present embodiment. It is to be noted that electrode lines are omitted in FIG. 10A and in FIG. 10B.

As expressed in Expression (6), mass m is expressed by material density ρ, thickness t, and area A of the electrode. For this reason, in the present embodiment, material density ρ, thickness t, and area A of the electrode are changed to adjust mass m among pMUT cells 200.

In pMUT cell 200 illustrated in FIG. 10A, the thickness of upper electrode 205a is increased in comparison with upper electrode 205 illustrated in FIG. 5B, for example.

In pMUT cell 200 illustrated in FIG. 10B, the diameter of upper electrode 205b is reduced in comparison with upper electrode 205 illustrated in FIG. 5B. That is, in FIG. 10B, the area of upper electrode 205b is reduced in comparison with FIG. 5B.

In addition, the density of the electrode material differs depending on the type of the electrode material of upper electrode 205.

As described, in pMUT cell 200, mass m is adjusted by changing the size or the material of the upper electrode of piezoelectric element 202. That is, mass m differs among pMUT cells 200 depending on material density ρ (not illustrated), thickness t (see FIG. 10A) or area A (see FIG. 10B) of the upper electrode of piezoelectric element 202.

Here, the variation of $\zeta$ in the case where mass m is changed in Expression (5) (Expression (7)) is expressed by the following expression.

[Expression 13]

$$\frac{\partial \zeta}{\partial m} = \frac{\partial \zeta}{\partial c_c} \frac{\partial c_c}{\partial m} = -\frac{c}{c_c^2} \sqrt{\frac{k}{m}} < 0 \tag{13}$$

From Expression (13), increase in mass m caused by the upper electrode of piezoelectric element 202 contributes to the positive change of $\zeta$ as illustrated in FIG. 10C.

By adjusting the shape or type of upper electrode 205 of piezoelectric element 202 among pMUT cells 200 in this manner, the phase characteristics ($\zeta$) of pMUT cells 200 can be substantially equalized.

Hereinabove, the methods of adjusting the phase characteristics using spring constant k, viscosity coefficient c, and mass m have been described.

For example, it is possible to substantially equalize the phase characteristics of pMUT cells 200 by adjusting at least two of the parameters of spring constant k, viscosity coefficient c, and mass m at the time of manufacturing of pMUT cell 200. For example, two of spring constant k, viscosity coefficient c, and mass m may be adjusted, or all of spring constant k, viscosity coefficient c, and mass m may be adjusted.

FIG. 11 shows an exemplary evaluation on parameters based on predetermined evaluation criteria in adjustment of phase characteristics. It should be noted that the method for setting the parameters used in adjustment of phase characteristics is not limited to the method illustrated in FIG. 11.

For example, FIG. 11 shows the case where length L, height h, and width b illustrated in FIGS. 8A and 8B are used as the parameters for setting spring constant k, and area A, thickness t, material density ρ of upper electrode 205 are used as the parameters for setting mass m. In addition, in FIG. 11, the following points (1) to (3) are used as the evaluation criteria for the parameters. Specifically, (1): the manageability of the accuracy in adjustment of the structure (shape, thickness and the like) of pMUT cell 200; (2): the simplicity of the structure of piezoelectric element 202 in its thickness direction, which has influences on the number of photomasks or lithography processes at the time of manufacturing; and (3): the amount of the material of pMUT cell 200.

In FIG. 11, evaluations of the parameters based on the evaluation criteria are determined by "A (excellent)" and "B (poor)," and the total score (the number of "A") is determined Here, it suffices that phase characteristics are substantially equalized among pMUT cells 200 by differently adjusting parameters of the highest total score among pMUT cells 200. For example, in FIG. 11, spring constant k is adjusted by length L and width b, and mass m is adjusted by area A of upper electrode 205, to thereby substantially equalize the phase characteristics of pMUT cells 200. Thus, the phase characteristics of pMUT cells 200 can be substantially equalized while preventing the manufacturing process from being complicated and preventing the quality of manufactured pMUT cells 200 from being degraded.

Thus, the use of a plurality of parameters (spring constant k, viscosity coefficient c, or, mass m) in each pMUT cell 200 can enhance the accuracy of adjustment of the phase characteristics (value of $\zeta$) in comparison with the case where only one parameter is used, for example.

Figure 12:
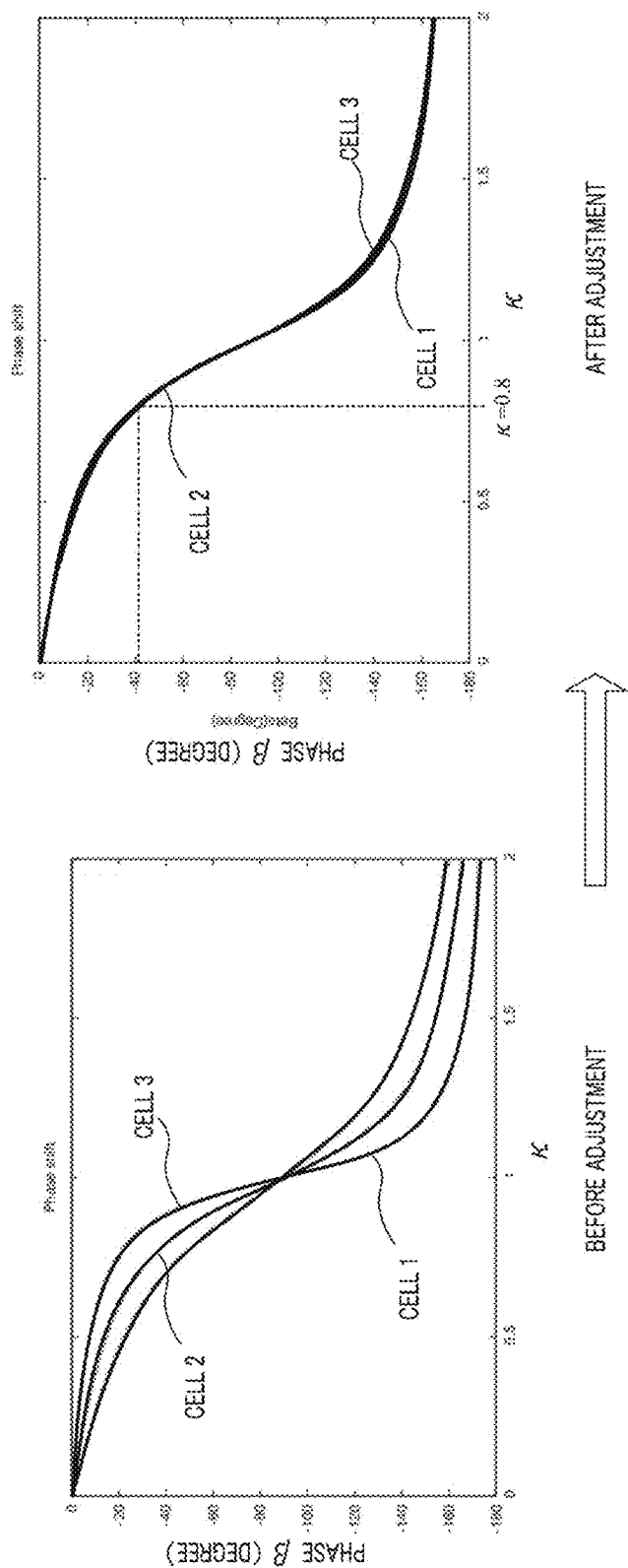
FIG. 12 shows a relationship between κ and phase β before and after adjustment of phase characteristics according to the present disclosure.

FIG. 12 shows exemplary phase characteristics of pMUT cell 200 (in FIG. 12, cells 1 to 3) before and after adjustment. As illustrated in FIG. 12, before adjustment, the phase characteristics of cells 1 to 3 are different from one another, and after adjustment, the phase characteristics of cells 1 to 3 are substantially the same.

At this time, it suffices to set κs (driving oscillation ratios) of pMUT cells 200 during the driving of ultrasound transducer 20 to the same value. For example, in FIG. 12, it suffices to drive pMUT cells 200 (cells 1 to 3) by frequencies that set κs to the same value. In this manner, the phases of pMUT cells 200 are set to substantially the same phases.

Figure 13B:
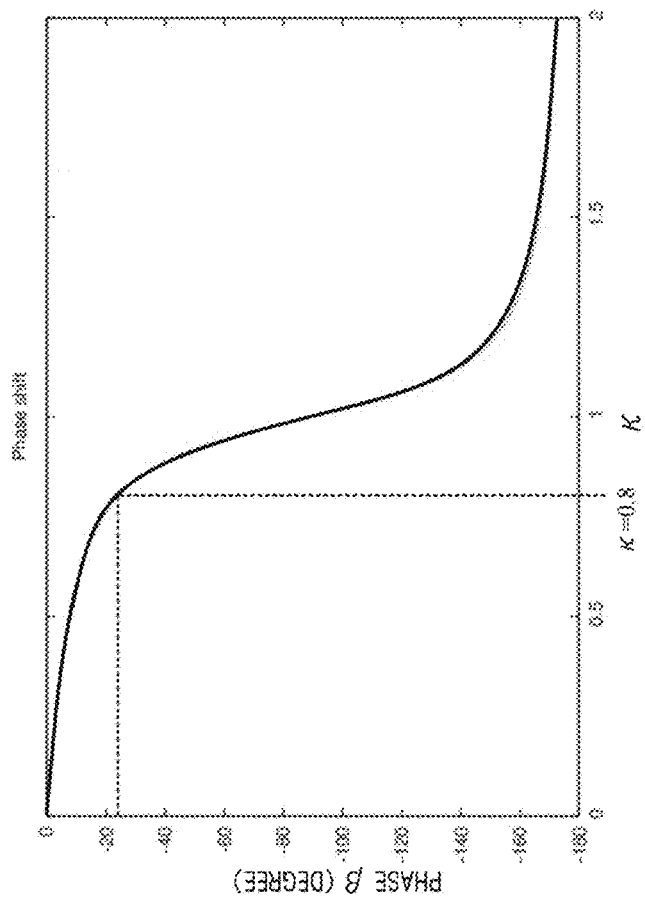
FIGS. 13A and 13B are an explanatory view and a graph in the case where the same κ is used in the pMUT cells according to the present disclosure.
Figure 13A:
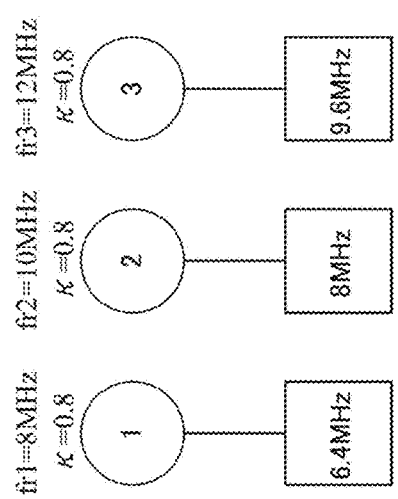

An exemplary case where resonance frequencies (fr1, fr2, and fr3) of cells 1 to 3 that are pMUT cells 200 are respectively 8 MHz, 10 MHz, and 12 MHz as shown in FIG. 13A is described. In this case, it is assumed that the phase characteristics of cells 1 to 3 are substantially equalized as illustrated in FIG. 13B. In addition, in this case, cells 1 to 3 are set to the same value of κ=0.8 as illustrated in FIG. 13B. In this case, as illustrated in FIG. 13A, cells 1 to 3 are driven by driving frequencies of 6.4 MHz, 8 MHz, and 9.6 MHz, respectively.

That is, as illustrated in FIG. 13B, the same phase β is obtained by using the same phase characteristics and the same value of κ for pMUT cells 200 having different resonance frequencies. That is, even when resonance frequencies (i.e., ωo) are different among pMUT cells 200, the phase characteristics (phases β) can be equalized among pMUT cells 200 by simultaneously driving pMUT cells 200 by driving frequencies (i.e., ω) that set κ (see Expression (4)) to the same value with substantially the same phase characteristics.

Thus, according to the present embodiment, even when a plurality of pMUT cells 200 are simultaneously driven, mutual cancellation of the output sound pressures of pMUT cells 200, which is caused by inversion of the phases of pMUT cells 200, is not caused, and consequently it is possible to prevent the output sound pressure of the entire ultrasound exchange section 22 from being dropped. That is, it is possible to prevent the sensitivity of ultrasound transducer 20 from being degraded.

It is to be noted that while κ=0.8 is used in each pMUT cell 200 in the present embodiment as illustrated in FIG. 13B, the value of κ used in pMUT cell 200 is not limited to 0.8, and, for example, a value of κ>1 may also be used.

In general, regarding the characteristics between κ and phase β (see, for example, FIG. 6), phase β has a constant value at κ=1 (ω=ω$_0$) regardless of the value of ζ, but the variation of phase β near κ=1 is abrupt. That is, the variation of phase β with respect to the variation of the value of κ is large near κ=1. On the other hand, as illustrated in FIG. 6, the smaller the value of κ (ω<<ω$_0$), or the greater the value of κ (ω>>ω$_0$), the smaller the amount of the variation of phase β with respect to the variation of the value of κ.

In addition, for example, the phase characteristics of pMUT cells 200 may not possibly be completely the same among pMUT cells 200 due to manufacturing errors and the like even when the structures of pMUT cells 200 are adjusted. In this case, if a value near κ=1 is used in pMUT cells 200, phase β differs among pMUT cells 200, and as a result, mutual cancellation of the output sound pressures cannot be avoided. In view of this, in the present embodiment, the value of κ used in pMUT cells 200 may have a value sufficiently smaller than κ=1 (e.g., near κ=0 in FIG. 6), or a value sufficiently larger than κ=1 (e.g., near κ=2 in FIG. 6). In this manner, the accuracy of adjustment of phases β of pMUT cells 200 is further enhanced. Thus, even when non-uniformity is caused after is adjusted in pMUT cells 200 and the phase characteristics are equalized, it is possible to prevent the phase difference among pMUT cells 200 due to the non-uniformity from being increased.

Figure 14B:
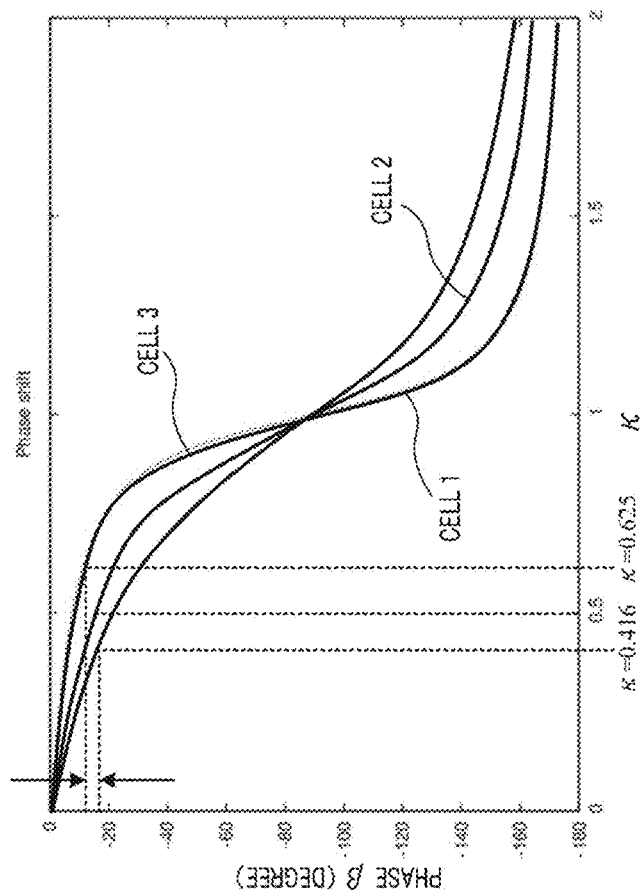
FIGS. 14A and 14B are an explanatory view and graph in the case where different κs are used in the pMUT cells according to the present disclosure.
Figure 14A:
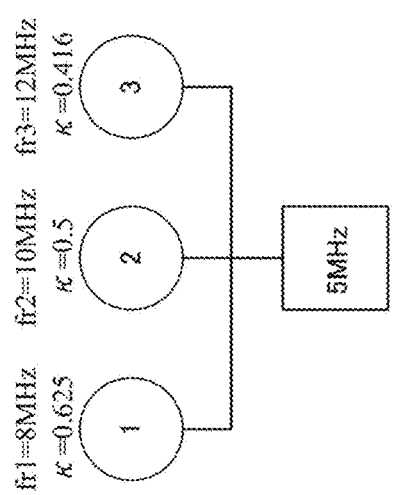

In addition, in the present embodiment, the values of κ used in pMUT cells 200 are the same value as illustrated in FIG. 13B. Alternatively, different values of κ may be used among pMUT cells 200. An exemplary case where the resonance frequencies (fr1, fr2, and fr3) of cells 1 to 3 that are pMUT cells 200 are respectively 8 MHz, 10 MHz, and 12 MHz as illustrated in FIG. 14A is described. In this case, the values of κ used in pMUT cells 200 may be set such that the difference of phases β (difference between the maximum value and the minimum value) among pMUT cells 200 (cells 1 to 3) is set to a value smaller than a predetermined threshold (for example, 20 degrees) as illustrated in FIG. 14B. For example, in FIG. 14B, cells 1 to 3 are driven at κ=0.625, 0.5, and 0.416, respectively. In this case, as illustrated in FIG. 13A, cells 1 to 3 are each driven by a driving frequency of 5 MHz. Thus, even when non-uniformity is caused after ζ is adjusted in pMUT cells 200 and the phase characteristics are equalized, it is possible to prevent the phase difference among pMUT cells 200 due to the non-uniformity from being increased.

In addition, as described above, the amount of the variation of phase β is small (i.e., phase difference is small) when value of κ is sufficiently smaller than κ=1 (e.g., near κ=0 in FIG. 6), or, sufficiently greater than κ=1 (e.g., near κ=2 in FIG. 6). Therefore, instead of κ=0.8 illustrated in FIG. 13B, a value near κ=0 or a value near κ=2 may be used for pMUT cells 200. In this manner, driving frequency (ω) can be set more freely while preventing the phase difference in pMUT cells 200 from being increased.

While an exemplary setting of the value of κ in pMUT cell 200 has been described, the above-mentioned exemplary setting of κ may be applied to each cell group unit composed of a predetermined number of pMUT cells 200.

INDUSTRIAL APPLICABILITY

The present disclosure is suitable for an ultrasound transducer having a plurality of pMUTs.

REFERENCE SIGNS LIST

1 Ultrasound diagnostic apparatus
10 Ultrasound diagnostic apparatus main body
11 Operation input section
12 Transmission section
13 Reception section
14 Image processing section
15 Display section
16 Control section
20 Ultrasound transducer
21 Protective layer
22 Ultrasound exchange section
23 Bucking material
24 Signal processing circuit 24
30 Cable
200 pMUT cell
201, 201a Substrate
202 Piezoelectric element
203 Piezoelectric thin film
204 Lower electrode
205, 205a, 205b Upper electrode
206 Filler
207 Resin material

The invention claimed is:

1. An ultrasound transducer including an array of a plurality of piezoelectric cells having resonance frequencies different from one another, wherein
the piezoelectric cells each include
a piezoelectric element, and
a substrate that supports the piezoelectric element, and
the piezoelectric cells each have a diaphragm structure with a support body comprising the substrate and a diaphragm comprising the piezoelectric element, the diaphragm exhibiting characteristics of a single damped oscillation model,
the piezoelectric element includes
a piezoelectric thin film,
a first electrode that is disposed on a first surface of the piezoelectric thin film in a thickness direction of the piezoelectric thin film and is joined on the substrate, and
a second electrode that is disposed on a second surface of the piezoelectric thin film in the thickness direction of the piezoelectric thin film and is paired with the first electrode to apply a voltage to the piezoelectric thin film, and
in each piezoelectric cell of the piezoelectric cells, at least two of parameters of a spring constant, a viscosity coefficient, and a mass in the single damped oscillation model of the diaphragm of the each piezoelectric cell are different from others of the piezoelectric cells and a relationship between a driving frequency ratio and a phase in the diaphragm of the each piezoelectric cell is substantially identical to the relationship between a driving frequency ratio and a phase in the diaphragm of the others of the piezoelectric cells.

2. The ultrasound transducer according to claim 1, wherein a hole is partially formed in a surface of the substrate at an outer periphery portion of the piezoelectric element, the surface being in contact with the piezoelectric element, and,
among the piezoelectric cells, the spring constant differs depending on a size of the hole.

3. The ultrasound transducer according to claim 1, wherein
the substrate has a hollow part that is a portion defined by projecting the piezoelectric element to the substrate in a thickness direction of the piezoelectric element, and,
among the piezoelectric cells, the viscosity coefficient differs depending on whether the hollow part is filled with a filler, or depending on a material of the filler.

4. The ultrasound transducer according to claim 1 further comprising an insulation layer that is formed to cover the piezoelectric element, wherein,
among the piezoelectric cells, the viscosity coefficient differs depending on a material of the insulation layer.

5. The ultrasound transducer according to claim 1, wherein, among the piezoelectric cells, the mass differs depending on a thickness of the second electrode.

6. The ultrasound transducer according to claim 1, wherein, among the piezoelectric cells, the mass differs depending on a diameter of the second electrode.

7. The ultrasound transducer according to claim 1, wherein, among the piezoelectric cells, the mass differs depending on a material of the second electrode.

8. An ultrasound diagnostic apparatus comprising:
an ultrasound transducer including an array of a plurality of piezoelectric cells having resonance frequencies different from one another;
a transmission section that drives the ultrasound transducer to transmit a first ultrasound signal to a test object;
a reception section that drives the ultrasound transducer to receive a second ultrasound signal from the test object in response to the first ultrasound signal;
an image processing section that creates an image for ultrasound diagnosis with use of the second ultrasound signal; and
a display section that displays the image created by the image processing section, wherein
the piezoelectric cells each include
a piezoelectric element, and
a substrate that supports the piezoelectric element,
the piezoelectric cells each have a diaphragm structure with a support body comprising the substrate and a diaphragm comprising the piezoelectric element, the diaphragm exhibiting characteristics of a single damped oscillation model, and
the piezoelectric element include
a piezoelectric thin film,
a first electrode that is disposed on a first surface of the piezoelectric thin film in a thickness direction of the piezoelectric thin film and is joined on the substrate, and
a second electrode that is disposed on a second surface of the piezoelectric thin film in the thickness direction of the piezoelectric thin film and is paired with the first electrode to apply a voltage to the piezoelectric thin film, and,
in each piezoelectric cell of the piezoelectric cells, at least two of parameters of a spring constant, a viscosity coefficient, and a mass in the single damped oscillation model of the diaphragm of the each piezoelectric cell are different from others of the piezoelectric cells and a relationship between a driving frequency ratio and a phase in the diaphragm of the each piezoelectric cell is substantially identical to the relationship between a driving frequency ratio and a phase in the diaphragm of the others of the piezoelectric cells.

9. The ultrasound diagnostic apparatus according to claim 8, wherein the driving frequency ratios of respective piezoelectric cells are identical to one another when the ultrasound transducer is driven.

10. The ultrasound diagnostic apparatus according to claim 9, wherein a value of each driving frequency ratio is smaller than one, or greater than one.

11. The ultrasound diagnostic apparatus according to claim 8, wherein
the driving frequency ratios of respective piezoelectric cells are different from one another when the ultrasound transducer is driven, and
a difference between a maximum phase and a minimum phase is smaller than a predetermined threshold in the piezoelectric cells.

* * * * *